United States Patent [19]

Terao et al.

[11] Patent Number: 4,925,868

[45] Date of Patent: May 15, 1990

[54] 4-HYDROXY-3-PYRROLIN-2-ONES AND TREATMENT OF CIRCULATORY DISORDERS THEREWITH

[75] Inventors: Shinji Terao; Minoru Hirata, both of Osaka, Japan

[73] Assignee: Takeda Chemical Industries, Ltd., Osaka, Japan

[21] Appl. No.: 84,177

[22] Filed: Aug. 12, 1987

[30] Foreign Application Priority Data

Aug. 29, 1986 [JP] Japan .................................. 61-204833

[51] Int. Cl.$^5$ ..................... C07D 207/38; A61K 31/40
[52] U.S. Cl. ..................................... 514/425; 548/544; 548/453
[58] Field of Search .......................... 548/544; 514/425

[56] References Cited

U.S. PATENT DOCUMENTS 3,401,176  9/1968  Hofmann et al. .................... 548/544

FOREIGN PATENT DOCUMENTS 2729903  1/1978  Fed. Rep. of Germany .

OTHER PUBLICATIONS

Tsuzuki, Kazuo, et al., "Sulfur-Extrusive Rearrangement of α-Acylthio Ester by Lithium Amide", *Bull. Chem. Soc. Jpn.*, vol. 58, pp. 395-396 (1985).
Schmierer, Roland, et al., "Cyclisierung von N-Acylalanin-und N-Acylglycinestern", *Liebigs Ann. Chem.*, pp. 1095-1098 (1985).
Schmidlin, Tibur, et al., "Approaches to the Synthesis of Cytochalasans. Part 2. Pyrrolinone Derivates as Basic Units$^1$)$^2$)", *Helvetica Chimica Acta*, vol. 63, pp. 121-131 (1980).
S. Suzuki, et al., "Studies on Antiviral Agents: Biological Activity of Tenuazonic Acid" *Chem. Pharm. Bull.* vol. 15, pp. 1120-1122 (1967).

*Primary Examiner*—David B. Springer
*Attorney, Agent, or Firm*—Wegner & Bretschneider

[57] ABSTRACT

The present invention relates to a compound of the formula:

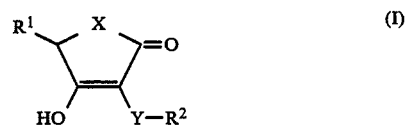

wherein X is sulfur or optionally substituted imino group; Y is a bond, oxygen, phenylene, phenyleneoxy, or oxyphenyleneoxy; $R^1$ is hydrogen or optionally substituted hydrocarbon residue; $R^2$ is optionally substituted hydrocarbon residue; and $R^1$ may form, together with the imino-nitrogen atom as X, a nitrogen-containing 5- to 7-membered ring, production and use thereof.

The compound (I) of the present invention has an antioxidation activity and activities of preventing or improving functional disorders due to biologically active oxygen species, thus being useful as a pharmaceutical agent for prophylaxis and therapy of disorders in the circulatory system.

15 Claims, No Drawings

4-HYDROXY-3-PYRROLIN-2-ONES AND TREATMENT OF CIRCULATORY DISORDERS THEREWITH

This invention relates to cyclic enol derivatives useful for therapy, prophylaxis and improvement of disorders in the circulatory system, and a method of preparing them.

Diseases of heart, brain, kidney, etc., which are often observed in adults, are in most cases accompanied with ischemia as a basal pathologic state. The morbidity rate of, for example, ischemic heart diseases, ischemic cerebral diseases, ischemic renal disturbances and ischemic gastro-intestinal ulcers, has recently increased with the development of highly civilized society, and of the society holding high rates of persons of advanced age, and these diseases have become major factors in mortality rate in advanced countries.

Recently, it has been revealed that leukocyte and active oxygen species or reactive organic radical species play an important role in aggravation of lesions in ischemic tissues, i.e. lowering of cell function, disturbances, destruction and necrosis of cells [I. Fridovich, Annual Review of Pharmacology and Toxicology 23, 239 (1983); J. M. McCord, The New England Journal of Medicine, 312, 159 (1985); K. P. Burton, J. M. McCord and G. Ghai, American Journal of Physiology, 246, H776 (1984)]. As the active oxygen species or reactive organic radical species in living systems are considered, among others, superoxide ($O_2^-\cdot$), hydroxyl radical ($\cdot OH$), singlet oxygen ($^1O_2$), and peroxide radical ($ROO\cdot$). It is considered that, especially, abnormal oxygen-absorption and excess generation of superoxide ($O_2^-\cdot$) occurring when blood is reperfused again after being once having been placed at the state of ischemia are causes of inviting disturbances on cells or tissues indiscriminately.

It has been known that superoxide dismutase effectively scavenges superoxide ($O_2^-\cdot$) and specifically protects against tissue damages and alleviates tissue disturbances after reperfusion of the site of ischemia or after ischemia [D. N. Granger, G. Rutili, J. M. McCord, Gastroenterology, 81, 82 (1981)]. Also, it has been reported that such compounds as ascorbic acid, α-tocopherol, cysteine and reduced glutathione have an activity to scavenge free radicals, and that these compounds could prevent lesions in tissues, which are supposedly caused by free radicals in certain pathological conditions [I. Fridovich, Science, 201, 875 (1978)].

Based on the biochemical and pharmacological fundamental studies so far made, revealing that active oxygen species and organic radical species play a significantly important role in causing tissue disturbances in a living system, especially those after reperfusion at the site of ischemic lesion in heart, brain, kidney, lung and digestive system, the present inventors have conducted research work for finding a novel type of pharmaceuticals excellent not only from the viewpoint of taking advantage of chemical synthesis but also pharmacological as well as pharmaceutical activity to scavenge active oxygen species and organic radical, as compared with the free radical scavengers mentioned above. As the result, the present inventors found that a certain type of cyclic enol derivatives showed, as compared with ascorbic acid, α-tocopherol, etc., stronger actions to scavenge active oxygen species and organic radical species, and that they controlled ischemic heart diseases, disturbances in cerebral function or renal disorders, thus accomplishing the present invention.

The present invention provides a compound of the formula:

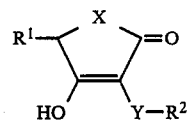

[wherein X is sulfur or an optionally substituted imino group; Y is a bond, oxygen, phenylene, phenylenoxy or oxyphenylenoxy; $R^1$ is hydrogen or an optionally substituted hydrocarbon residue; $R^2$ is an optionally substituted hydrocarbon residue; and $R^1$ may form, together with the imino-nitrogen as X, a nitrogen-containing 5- to 7-membered ring], and a method of preparing a compound (I), characterized by subjecting a compound representable by the formula:

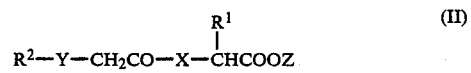

[wherein X, Y, $R^1$ and $R^2$ are of the same meaning as defined above, and Z is a lower alkyl] to cyclization in the presence of a base.

The substituent of the optionally substituted imino group represented by X is a hydrocarbon residue such as alkyl, alkenyl, alkynyl, aryl, aralkyl, etc. or a heterocyclic ring such as thienyl, etc. or a heterocyclyl-alkyl group. The alkyl includes those of 1 to 15 carbon atoms, such as, for example, methyl, ethyl, n-propyl, isopropyl, n-butyl, isobutyl, n-pentyl, n-hexyl, n-heptyl, n-octyl, n-nonyl, n-decyl, n-undecyl, dodecyl, etc. which may have one or more substituent (e.g. hydroxyl, $C_{1-3}$alkoxy, halogen, carboxy, $C_{1-3}$alkoxycarbonyl); the alkenyl includes those of 2 to 5 carbon atoms, such as, for example, vinyl, allyl, isopropenyl, etc.; the alkynyl includes those of 2 to 5 carbon atoms, such as, for example, ethynyl, 2-propynyl, 2-butynyl, etc.; the aryl includes phenyl optionally having one or more substituents (e.g hydroxyl, $C_{1-6}$alkyl, halogen, trihalogenomethyl, $C_{1-3}$alkoxy, methylenedioxy, etc.), such as, for example, phenyl, 3-trifluoromethylphenyl, 4-hydroxyphenyl, 4-methoxyphenyl, 4-dihydroxyphenyl, etc.; the aralkyl includes phenyl $C_{1-3}$alkyl or naphtyl $C_{1-3}$alkyl optionally having one or more substituents (e.g. halogen, trihalogenomethyl, methylenedioxy, $C_{1-3}$alkyl, $C_{1-3}$alkoxy, $C_{1-3}$alkoxycarbonyl, carboxyl, etc.), such as, for example, benzyl, 3,4,5-trimethoxybenzyl, 2,5-dimethoxy-3,4,6-trimethylbenzyl, 3,4-dimethoxybenzyl, 3,4-methylenedioxybenzyl, 4-ethoxycarbonylbenzyl, 4-carboxybenzyl, phenethyl, phenylpropyl, 4-chlorobenzyl, 3-trichloromethylbenzyl, 2-, 3-, or 4-chlorobenzyl, 1- or 2-naphthylmethyl, etc.; and the heterocyclic ring or heterocyclyl-alkyl includes 2-thienyl, 3-thienylmethyl, etc.

The nitrogen-containing 5- to 7-membered ring which may be formed by the imino-nitrogen together with a hydrocarbon residue optionally containing a sulfur atom, of $R^1$, is preferably exemplified by such group as pyrrolidine, piperizine, hexamethyleneimine, thiazolidine etc., which may have substituents (e.g. hydroxyl, $C_{1-3}$alkyl, carboxyl).

As to phenylene, phenyleneoxy and oxyphenyleneoxy for Y (a spacer), o-, m- or p-phenylene, o-, m- or p-phenyleneoxy and o-, m- or p-oxyphenyleneoxy may be respectively exemplified. Specifically preferable Y is a bond, p-phenylene, o-, m- or p-phenylenoxy or an oxygen atom.

The hydrocarbon residue shown by $R^1$ is exemplified by lower ($C_{1-6}$) alkyl, lower ($C_{2-6}$) alkenyl, lower ($C_{2-6}$) alkynyl, aryl, etc., and these groups may optionally be substituted.

The above-mentioned lower alkyl groups are exemplified by optionally substituted straight-chain or branched alkyl groups. The alkyl groups in the straight-chain or branched alkyl groups are exemplified by methyl, ethyl, propyl, iso-propyl, n-butyl, iso-butyl, n-pentyl, n-hexyl, etc. and preferably $C_1$–$C_3$ lower alkyl groups.

The above-mentioned lower alkenyl is preferably $C_2$–$C_4$ lower alkenyl, as exemplified by ethenyl, 1- or 2-propenyl, isopropenyl, 1-, 2- or 3-butenyl, etc.

The above-mentioned lower alkynyl is preferably $C_2$–$C_4$ lower alkynyl, as exemplified by ethynyl, 1- or 2-propynyl, 1, 2- or 3-butynyl, etc.

The above-mentioned aryl is exemplified by phenyl, naphthyl, etc.

These hydrocarbon residues may optionally have one to three identical or different substituents, which are exemplified by optionally substituted hydroxyl, $C_1$–$C_3$ lower alkylthio, optionally substituted phenylthio, optionally substituted phenyl, vinyl, optionally substituted ethynyl and $C_{1-3}$alkoxycarbonyl. As substituents of the optionally substituted hydroxyl group are mentioned methyl, ethyl, n-propyl, isopropyl, allyl, propargyl, phenyl, etc.; as substituents of the phenyl group of the optionally substituted phenylthio group and the optionally substituted phenyl group are mentioned hydroxyl, methoxy, fluoro, etc.; and as substituents of the optionally substituted ethynyl group are mentioned methyl, ethyl, phenyl, etc.; respectively.

Especially preferable ones among the groups shown by $R^1$ include hydrogen atom, lower ($C_{1-3}$)alkyl optionally substituted with hydroxyl, carboxy, $C_{1-3}$alkoxycarbonyl or/and phenyl and phenyl optionally substituted with hydroxyl or carboxyl.

Referring to $R^2$ in the compound (I), the hydrocarbon having two or more carbon atoms is exemplified by alkyl, alkenyl, alkynyl or aralkyl, and those of 6 to 20 carbon atoms are preferably. In the case of alkenyl or alkynyl, those having 1 to 4 unsaturated bond (double or triple bond) are preferable.

The above-mentioned alkyl is exemplified by n-propyl, isopropyl, n-butyl, isobutyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, etc.

The above-mentioned alkenyl is exemplified by 7-hexadecenyl, 9-octadecenyl, 9,12-octadecadienyl, 9,12-octadecadienyl, 9,12,15-octadecatrienyl, 8,11,14-eicosatrienyl, 5,8,11,14-eicosatetraenyl, etc.

The above-mentioned alkynyl is exemplified by 6-octynyl, 8-decynyl, 10-dodecynyl, 12-tetradecynyl, 14-hexadecynyl, 16-octadecynyl, etc.

Among these alkyl, alkenyl and alkynyl groups those having 9 to 20 carbon atoms are especially preferable.

The above-mentioned aralkyl is exemplified by phenyl-$C_{1-3}$alkyl or naphthyl-$C_{1-3}$alkyl which may have substituent (e.g. halogen, $C_{1-3}$alkyl, $C_{1-3}$alkoxy), e.g. benzyl, p-chlorobenzyl, p-fluorobenzyl, p-methylbenzyl, phenethyl, phenylpropyl, phenylbutyl, diphenylmethyl, 2,2-diphenylethyl, 1-naphthylethyl, 2-naphthylethyl, etc.

The compound (I) of the present invention can be prepared by, for example, subjecting a compound (II) to cyclization in the presence of a base.

Examples of the above-mentioned base (basic condensing agent) include inorganic bases such as alkali metal hydrides (e.g. sodium hydride), organic metal bases such as organic alkali metals (e.g. potassium tertiary butoxide, lithium diisopropylamide), etc., and as the solvent are mentioned organic solvents such as alcohols (e.g. tertiary butanol), ethers (e.g. dioxane, tetrahydrofuran), amides (e.g. N,N-dimethylformamide, hexamethylphophoramide), etc. The reaction temperature ranges from 0° C. to 70° C., and the reaction is completed in about 1 to 8 hours.

The starting compound (II) can be prepared by, for example, the following steps.

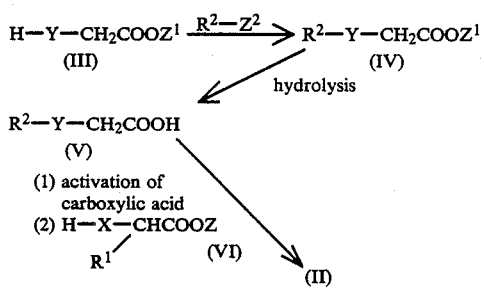

[wherein X, Y, Z, $R^1$ and $R^2$ are of the same meaning as defined above, $Z^1$ stands for lower alkyl, and $Z^2$ stands for halogen respectively].

The above-mentioned steps comprise allowing, for example, acetic acid ester (III) to react with halogenated hydrocarbon ($R^2$–$Z^2$) in the presence of a base to give a compound (IV), subjecting the compound (IV) to alkali hydrolysis to give a carboxylic acid derivative (V), then allowing this carboxylic acid derivative to react with a compound (VI) to give the intermediate (II).

In the above-mentioned steps, the base which may be employed for the production of the compound (IV) is exemplified by potassium carbonate, sodium carbonate, sodium hydride, etc., and the solvent is exemplified by methanol, ethanol, dimethyl sulfoxide, dimethylformamide, dioxane, tetrahydrofuran, etc. The compound (IV) is subjected to alkali hydrolysis by conventional means, followed by rendering pH of the hydrolyzate to acidic to thereby obtain the free carboxylic acid derivative (V).

In the case of X being an optionally substituted imino group, the carboxyl group of the compound (V) is activateted by a per se conventional method to thereby make an amide-linkage with an N-substituted glycine ester (VI) to give the intermediate (II). For activation of the carboxyl group in this reaction step, use is made of such methods as conversion of it into the corresponding acid chloride, mixed acid anhydrides, active esters, etc., which are usually prepared just prior to use. In the amide-linkage formation, use is made of an inorganic or organic base such as potassium carbonate, sodium carbonate, sodium hydroxide, pyridine, triethylamine, etc. As the reaction solvent, use is made of water or methanol, ethanol, acetone, tetrahydrofuran, acetonitrile, etc., singly or as a mixture with water.

In the case of X being sulfur atom, the carboxyl group of the compound (V) is activated by a per se known method, and allowed to react with an α-substituted thioglycolic acid ester (VI) to give the intermediate (II). For activation of the carboxyl group, use is made of conventional methods in which the carboxyl group is converted into the corresponding acid chloride, mixed acid anhydrides, active esters, etc. Thioesterification is conducted in an organic solvent (e.g. acetone, tetrahydrofuran, acetonitrile, etc.) in the presence of a base such as potassium carbonate, triethylamine, etc.

Thus prepared compound (I) can be isolated by per se conventional means (e.g. silica gel chromatography, recrystallization, etc.).

The compounds (I) of this invention show active oxygen species scavenging action in the experiments in vitro employing brain homogenates of rats, and, in the ischemia-reperfusion model in the heart of rats or the ischemic brain model in rats or the renal failure model in rats due to oxygen free radicals; they show actions of preventing or improving the respective functional disorders, while they show remarkably low toxicity and very little side effects. The compound (I) of this invention shows therapeutic, prophylactic and improving actions against various functional disorders in mammals (e.g. mouse, rat, rabbit, dog, monkey, human, etc.), for example, ischemic heart diseases (arrhythmia, coronary vasospasm, necrosis of cardiac tissue, myocardial infarction, etc.), subarachnoidal hemorrhage, ischemic disorders of cerebral tissue (e.g. cerebral infarction, dementia, etc.), ischemic renal disorders, ischemic intestinal disorders (e.g. intestinal ulcer, etc.), thus being useful as preventing and improving agents of functional disorders in the circulatory system.

Specific examples of the use mentioned above as the preventing and improving agents of functional disorders in the circulatory system include these for anti-arrhythmia, anti-myocardial infarction, anti-cerebral infarction, agents of preventing dementia, senile dementia, agents of therapy and improvement after subarachnoidal hemorrhage, improving agents of renal functions, therapeutic agents of stress, intestinal ulcer, etc.

The compounds of the present invention are of low toxicity: in an acute toxicity test in mice, no test animals were killed by oral administration of the compound at a dose of 1000 mg/kg. The compound (I) of the present invention can be safely administered orally or non-orally as pharmaceutical compositions [e.g. tablets, capsules (including soft-capsules and micro-capsules), liquids, suppositories, injections, preparations for nasal inhalation] prepared by mixing with per se conventional pharmacologically acceptable carriers, excipients, diluent, etc. in accordance with per se known methods. While the dosage varies with the subjects, administration routes, symptoms, etc., it is usually, when administered to the above-mentioned mammals, in terms of the compound (I), about 0.1 mg/kg to 50 mg/kg body weight, preferably about 0.5 mg/kg to 20 mg/kg body weight 1 to 3 times a day.

When the compound (I) is administered non-orally, for example, as a suppository, about 5 mg to 10 mg/kg in terms of the compound (I) is administered 1 to 2 times a day, and as an injection, about 0.1 mg/kg to 5 mg/kg in terms of the compound (I) is desirably used 1 to 2 times a day.

For preparation of the above-mentioned compositions for oral use, for example tablets, a binding agent (e.g. hydroxypropyl cellulose, hydroxymethylpropylmethyl cellulose, macrogol, etc.), a disintegrator (e.g. starch, carboxymethyl cellulose calcium, etc.), an excipient (e.g. lactose, starch, etc.) or a lubricant (e.g. magnesium stearate, talc, etc.), etc. may be suitably incorporated.

When a composition for non-oral use, for example an injectable preparation, is prepared, an isotonizing agent (e.g. glucose, D-sorbitol, D-mannitol, sodium chloride, etc.), an antiseptic (e.g. benzyl alcohol, chlorobutanol, methyl para-hydroxybenzoate, propyl para-hydroxybenzoate, etc.) or a buffer (e.g. phosphate buffer, sodium acetate buffer, etc.), etc. may be suitably incorporated.

EXPERIMENT 1

Activity to inhibit lipid peroxide formation in rat brain tissue homogenate:

(i) Method:

Male SD rats (12-week-old) were subjected to exsanguination under anesthesia with pentobarbital, then the brain was excised. The brain tissue was homogenized in a phosphate buffer (pH 7.4) to prepare a 5% homogenate. After incubation of the homogenate at 37° C. for 1 hour, the amount of lipid peroxides formed therein was determined by the thiobarbituric acid (TBA) method in accordance with the report of Ohkawa et al. on Analytical Biochemistry, 95, 351, (1979).

The test drug was added to the 5% homogenate before incubation so as to make the final concentration to be $10^{-5}$M. The activity to inhibit the formation of lipid peroxide was judged by comparing the amount of the lipid peroxide in the treated group with that of the reference group to which was added the solvent (DMSO), and shown by % inhibition. (ii) The results are shown in Table 1.

TABLE 1

| Activities to inhibit lipid peroxide formation in rat brain tissue homogeneates (TBA method) | |
|---|---|
| Compound | Inhibition rate (%)* |
| 4-a | 97.9 |
| 4-b | 97.9 |
| 4-c | 100 |
| 4-d | 100 |
| 4-e | 100 |
| 4-f | 75.5 |
| 4-g | 100 |
| 4-h | 100 |
| 4-i | 89.4 |
| 4-j | 52.8 |
| 4-k | 63.8 |
| 4-l | 96.7 |
| 4-m | 100 |
| 4-n | 100 |
| 4-o | 100 |
| Vitamin C | −71.6 |
| Vitamin E | 44.9 |

*(Note) The concentration of each compound is $10^{-5}$M, and the number of experiments of each compound is 3. Inhibitory effects (%) are shown by mean values.

EXPERIMENT 2

Activity to inhibit occurrence of ventricular arrhythmia during coronary artery occlusion-reperfusion in rat hearts (i) Method Male SD rats (9- to 13-week old, 250 to 370 g) were used. The animals were subjected to thoractonomy under artificial respiration while anesthesia was maintained by administering pentobarbital. The left anterior descending coronary artery was ligated with silk thread for 5 minutes, then the ligation was released to allow reperfusion, and the animals were observed for 10 minutes. By recording standard limb lead II electrocardiograms, occurrence of ventricular arrhythmia was examined.

The animals were treated, under non-anesthesia, with test drugs as a gum arabic suspension at the dosage of 10 mg/kg at the time of about 180 minutes prior to the closure of coronary artery. The results are shown in Table 2.

(ii) Results

When perfusion was resumed after the closure of the left anterior descending coronary artery for 5 minutes, ventricular arrhythmia, typically exemplified by occasionally occurring premature ventricular contractions (PVCs), ventricular tachycardia (VT) and ventricular fibrillation (VF), were observed. VT and VF were paroxysmally repeated, or sustained VF resulted in death.

In the group treated with the vehicle (control), VF and VT were observed in more than 90% of the animals, and the durations were respectively about 80 and 20 to 30 seconds. Among the animals, 10 to 25% were killed by occurrence of sustained VF.

In the groups treated with 10 mg/kg each of compound (4-1) and (4-p), occurrence of those types of arrhythmia was suppressed remarkably. Even when arrhythmia occurred, the period of time during which the symptom lasted was shortened. Consequently, the mortality due to VF was low. Frequency of occasional PVCs was around 10 times/minute in the group of the vehicle, while in the groups each treated with compound (4-1) and (4-p), the frequency was significantly less.

On the other hand, no significant effect was observed by oral diminstration of vitamin C or E at the dosage of 50 mg/kg.

Incidences of ventricular fibrillation and ventricular tachycardia are shown by the percentage of the number of animals presenting the symptoms relative to the number of animals subjected to the test, and the duration of the symptoms was shown by average ±SEM in seconds. Extrasystole is shown by the number of systole/min., and the mortality is shown by the percentage of the number of killed animals relative to the number of test animals.

TABLE 2

Effects on ventricular arrhythmias observed when reperfusion was permitted after closure of the coronary artery in rat hearts

| Group | Ventricular fibrillation | | Ventricular tachycardia | | | |
|---|---|---|---|---|---|---|
| | Incidence (10 min.) | Duration (sec.) | Incidence (10 min.) | Duration (sec.) | Extrasystole (times/min.) | Mortality |
| Control | 4.1 ± 0.7 | 74.2 ± 30.8 | 11.5 ± 5.0 | 26.5 ± 6.8 | 11.0 ± 4.0 | 2/18 |
| Compound (4-1) (3 mg/Kg) | 0.8 ± 0.4 | 1.7 ± 1.2 | 3.5 ± 0.8 | 7.1 ± 2.2 | 5.4 ± 1.1 | 0/8 |
| Compound (4-p) (10 mg/Kg) | 0.9 ± 0.3 | 2.1 ± 1.3 | 4.1 ± 1.2 | 7.3 ± 2.4 | 3.3 ± 0.7 | 0/9 |
| Vitamin C 50 mg/kg | 5.4 ± 0.8 | 74.1 ± 36.0 | 9.5 ± 1.8 | 12.0 ± 2.9 | 11.0 ± 0.8 | 1/12 |
| Vitamin E 50 mg/kg | 2.0 ± 0.7 | 43.4 ± 36.0 | 3.7 ± 1.5 | 22.3 ± 9.7 | 7.0 ± 4.1 | 1/10 |

EXPERIMENT 3

Acute toxicity in mice (i) Method

Male Crj-ICR mice (4-week-old, 21 to 26 g) were used. The animals, divided into groups, each consisting of six mice, were administered orally with compounds (4-b, 4-1) at the dosages of 300 and 1000 mg/kg, respectively. Then, each group was housed in a cage and observed for 24 hours.

The test drugs were suspended in gum arabic and administered at a volume of 0.1 ml/10 g.

(ii) Results

In both groups treated with compounds (4-b, 4-1) at the dosages of 300 and 1000 mg/kg, respectively, the state of sedation and ptosis were observed on half number of the test animals, but they had recovered within 3 hours. During 24-hour-observation, no test animals of either group were killed.

REFERENCE EXAMPLE 1

To a dimethylformamide (DMF, 100 ml) solution of ethyl 4-hydroxyphenylacetate (18 g, 0.1 mol.) and dodecyl bromide (25 g, 0.1 mol.) was added potassium carbonate (15 g, 0.1 mol.). The mixture was stirred at 100° C. for one hour. To the reaction solution, after cooling, was added water (200 ml) and the mixture was subjected to extraction with isopropyl ether (IPE). The organic layer was washed with water, dried and concentrated under reduced pressure. The concentrate was dissolved in a mixture of methanol (100 ml) and tetrahydrofuran (THF, 100 ml). To the solution was added aqueous sodium hydroxide (10 g, 0.25 mol.), and the mixture was stirred at 50° C. The reaction solution was concentrated under reduced pressure, whose pH was adjusted to 4, followed by extraction with ethyl acetate. The organic layer was washed with water, dried and concentrated under reduced pressure to leave crude crystals. Recrystallization from hexane-IPE gave 4-dodecyloxyphenylacetic acid (1-e, 20 g, 63%).

By the same procedure as above, compounds (1-a to 1-d and 1-f to 1-k) were synthesized. Physico-chemical properties and NMR spectra of these compounds are shown in Table 3.

TABLE 3

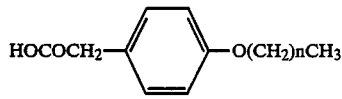

| Compd. | n | formula MP(°C.) | NMR spectrum (in CDCl$_3$, δ:ppm) | yield (%) |
|---|---|---|---|---|
| 1-a | 4 | C$_{13}$H$_{15}$O$_3$ 75–76 | 7.17(2H, d, 9Hz), 6.85(2H, d, 9Hz), 3.92(2H, t, 7Hz), 3.56(2H, s), 1.76 (2H, m), 1.39(4H, s), 0.92(3H, m) | 53 |
| 1-b | 6 | C$_{15}$H$_{22}$O$_3$ 79–80 | 7.19(2H, d, 9Hz), 6.85(2H, d, 9Hz), 3.92(2H, t, 7Hz), 3.54(2H, s), 1.75(2H, m), 1.34(8H, m), 0.88(3H, m) | 89 |
| 1-c | 9 | C$_{18}$H$_{28}$O$_3$ 69–70 | 7.16(2H, d, 9Hz), 6.82(2H, d, 9Hz), 3.91(2H, t, 7Hz), 3.55(2H, s), 1.74 (2H, m), 1.26(14H, s), 0.87(3H, m) | 70 |
| 1-d | 10 | C$_{19}$H$_{30}$O$_3$ 85–86 | 7.17(2H, d, 9Hz), 6.83(2H, d, 9Hz), 3.91(2H, t, 7Hz), 3.54(2H, s), 1.70 (2H, m), 1.27(16H, s), 0.87(3H, m) | 75 |
| 1-e | 11 | C$_{20}$H$_{32}$O$_3$ 81–82 | 7.10(2H, d, 9Hz), 6.84(2H, d, 9Hz), 3.92(2H, t, 7Hz), 3.63(2H, s), 1.70 (2H, m), 1.29(18H, s), 0.87(3H, m) | 63 |
| 1-f | 13 | C$_{22}$H$_{36}$O$_3$ 84–85 | 7.16(2H, d, 9Hz), 6.82(2H, d, 9Hz), 3.90(2H, t, 7Hz), 7.54(2H, s), 1.70 (2H, m), 1.26(22H, s), 0.85(3H, m) | 71 |
| 1-g | 17 | C$_{26}$H$_{44}$O$_3$ 80–81 | 7.18(2H, d, 9Hz), 6.83(2H, d, 9Hz), 3.92(2H, t, 7Hz), 3.57(2H, s), 1.75 (2H, m), 1.25(30H, s), 0.88(3H, m) | 68 |

TABLE 3 (II)

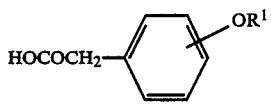

| Compd. | Position | R$^1$ | MP(°C.) | NMR spectrum (in CDCl$_3$ δ:ppm) |
|---|---|---|---|---|
| 1-h | m | (CH$_2$)$_{11}$CH$_3$ | C$_{20}$H$_{32}$O$_3$ 77–78 | 7.20(1H, m), 6.82(3H, m), 3.92(2H, t, 6Hz), 3.58(2H, s), 1.75(2H, m), 1.25(18H, m), 0.87(3H, m) |
| 1-i | m | Bz | C$_{15}$H$_{14}$O$_3$ 124–125 | 7.35(6H, m), 6.87(3H, m), 5.08(2H, s), 3.59(2H, s) |
| 1-j | p | (4-MeO)Bz | C$_{16}$H$_{16}$O$_4$ 157–158 | 7.32(2H, d, 9Hz), 7.22(2H, d, 9Hz), 6.92(4H, m), 4.97(2H, s), 3.80(3H, s), 3.57(2H, s) |
| 1-k | p | (4-F)Bz | C$_{15}$H$_{13}$O$_3$F 124–125 | 7.30(4H, m), 7.10(2H, d, 8Hz), 6.91(2H, d, 8Hz), 5.01(2H, s), 3.57(2H, s) |

REFERENCE EXAMPLE 2

To an ethanol solution (50 ml) of 3,4,5-trimethoxybenzaldehyde (2 g, 10 mmol.) and glycine ethyl ester hydrochloride (1.4 g, 10 mmol.) were added sodium hydrogencarbonate (1 g, 12 mmol.) and 5% - palladium on carbon (0.3 g). The reaction solution was stirred for 16 hours at 50° C. under 1 atmosphere pressure of hydrogen. The reaction solution, after cooling, was subjected to filtration to remove the catalyst, and the filtrate was concentrated under reduced pressure. The concentrate was purified by means of a silica gel chromatography (developing solvent: IPE:ethyl acetate=1:1) to afford ethyl N-(3,4,5-trimethoxybenzyl)aminoacetate (2-h, 1.5 g, 47%). Physico-chemical properties and NMR spectrum of this product are shown in Table 4.

REFERENCE EXAMPLE 3

To a DMF solution (50 ml) of 4-chlorobenzyl bromide (4.2 g, 20 mmol.) and glycine ethyl ester hydrochloride (2.8 g, 20 mmol.) was added potassium carbonate (5 g). The mixture was stirred at 60° C. for 3 hours. To the reaction solution, after cooling, was added water (100 ml), and the mixture was subjected to extraction with ethyl acetate. The organic layer was washed with water, dried and concentrated under reduced pressure. The concentrate was purified by means of a silica gel chromatography (developing solvent: IPE:ethyl acetate=1:1) to afford ethyl N-(4-chlorobenzyl) aminoacetate (2-j, 2.7 g, 60%). Physico-chemical properties and NMR spectrum of this product are shown in Table 4.

REFERENCE EXAMPLE 4

To an ethanol solution (50 ml) of methyl 4-formylbenzoate (6.4 g, 40 mmol.) and glycine ethyl ester hydrochloride (5.6 g, 40 mmol.) was added potassium carbonate (5.6 g, 40 mmol.), and the mixture was stirred at room temperature for one hour. To the reaction solution was added sodium cyanoborohydride (2 g, 50 mmol.), and the mixture was stirred for further 18 hours. The reaction solution was subjected to filtration, and the filtrate was concentrated under reduced pressure. To the concentrate was added water (50 ml), and the mixture was subjected to extraction with ethyl acetate. The organic layer was washed with water, dried and concentrated under reduced pressure. The concentrate was purified by means of a silica gel chromatography (developing solvent: IPE:ethyl acetate=1:1) to afford ethyl N-(4-methoxycarbonylbenzyl)aminoacetate (2-g, 5 g, 50%).

By the same procedure as above, compounds (2-a to 2-f and 2-i) were synthesized. Physico-chemical properties and NMR spectra of these compounds are shown in Table 4.

TABLE 4

$R^1\text{NHCH}_2\text{COOEt}$

| Compd. | $R^1$ | formula MP(°C.) | NMR spectrum (in CDCl$_3$, TMS internal std. δ:ppm) | Ref. Ex. referred |
|---|---|---|---|---|
| 2-a | Me₂CHCH₂— | C$_8$H$_{17}$NO$_2$ | 4.18(2H, q, 7Hz), 3.38(2H, s), 2.40(2H, d, 7Hz), 1.77 (1H, m), 1.27(3H, t, 7Hz), 0.91(6H, d, 7Hz) | 2 |
| 2-b | Me(CH$_2$)$_{11}$— | C$_{16}$H$_{33}$O$_2$ | 4.18(2H, q, 7Hz), 3.37(2H, s), 2.58(2H, m), 1.26(23H, m), 0.86(3H, m) | 3 |
| 2-c | Bz— | C$_{11}$H$_{15}$NO$_2$ | 7.27(5H, s), 4.17(2H, q, 7Hz), 3.76(2H, s), 3.35(2H, s), 1.23(3H, t, 7Hz) | 4 |
| 2-d | Ph-CH$_2$CH$_2$— | C$_{12}$H$_{17}$NO$_2$ | 7.24(5H, s), 4.15(2H, q, 9Hz), 3.38(2H, s), 2.83(4H, m), 1.24(3H, t, 7Hz) | 3 |
| 2-e | Ph-(CH$_2$)$_3$— | C$_{13}$H$_{19}$NO$_2$ | 7.22(5H, s), 4.16(2H, q, 7Hz), 3.36(2H, s), 2.68(4H, m), 1.84(2H, m), 1.24(3H, t, 7Hz) | 3 |
| 2-f | 3-thienyl-CH$_2$— | C$_9$H$_{13}$NO$_2$S | 7.20(3H, m), 4.17(2H, q, 7Hz), 3.82(2H, s), 3.39(2H, s), 1.25(3H, t, 7Hz) | 4 |
| 2-g | MeOCO-C$_6$H$_4$-CH$_2$— (4-) | C$_{13}$H$_{17}$NO$_4$ | 7.98(2H, d, 9Hz), 7.39(2H, d, 9Hz), 4.18(2H, q, 7Hz), 3.88(5H, s), 3.37(2H, s), 1.25(3H, t, 7Hz) | 4 |
| 2-h | (3,4,5-MeO)Bz— | C$_{13}$H$_{21}$NO$_5$ | 6.59(2H, s), 4.20(2H, q, 7Hz), 3.85(9H, s), 3.40(2H, s), 1.27(3H, t, 7Hz) | 4 |
| 2-i | 2,3,5-Me$_3$-4,6-(OMe)$_2$-C$_6$-CH$_2$— | C$_{16}$H$_{25}$NO$_4$ | 4.17(2H, q, 7Hz), 3.83(2H, s), 3.70(3H, s), 3.64(3H, s), 2.30(3H, s), 2.17(6H, s), 1.26(3H, t, 7Hz) | 2 |
| 2-j | (4-Cl)Bz— | C$_{11}$H$_{14}$NO$_2$Cl | 7.28(4H, s), 4.16(2H, q), 3.75(2H, s), 3.36(2H, s), 1.24(3H, t, 7Hz) | 3 |

REFERENCE EXAMPLE 5

To a dichloromethane solution (50 ml) of 4-dodecylphenylacetic acid (3.2 g, 0.01 mol.) was added dropwise oxalyl chloride (2ml). The reaction was allowed to proceed for 30 minutes at room temperature. The reaction solution was stirred at 50° C. for further 30 minutes, followed by concentration under reduced pressure. The concentrate was dissolved in dichlormethane (10 ml), which was added dropwise at 0° C. to a solution prepared by dissolving N-methyl glycine ethylester hydrochloride (1.6 g, 0.01 mol.) in a mixture of dichloromethane (50 ml) and trimethylamine (4 ml). The reaction solution was stirred at room temperature for one hour, to which was added IPE (100 ml), followed by washing with water. The organic layer was dried and concentrated under reduced pressure. The concentrate was purified by means of a silica gel chromatography (developing solvent: IPE:ethyl acetate=1:1) to afford ethyl N-(4-dodecyloxyphenylacetyl)-N-methylaminoacetate (3-i, 4.0 g, 95%).

By the procedure as above, analogues (3-a to 3-o) were synthesized. Physico-chemical properties and NMR spectra of them are in Table 5 and Table 6.

TABLE 5

$$\text{CH}_3(\text{CH}_2)_n\text{O}-\text{C}_6\text{H}_4-\text{CH}_2\text{CON}(R^1)\text{CH}_2\text{COOEt}$$

| Compd. | n | $R^1$ | formula | NMR spectrum (in CDCl$_3$, δ: ppm) |
|---|---|---|---|---|
| 3-a | 11 | CH$_3$(CH$_2$)$_{11}$— | C$_{36}$H$_{63}$NO$_4$ | 7.17(2H, m), 6.83(2H, m), 4.17(2H, q, 7Hz), 4.04: 3.98(2H, s), 3.92(2H, t, 7Hz), 3.70:3.30(2H, m), 1.65(2H, m), 1.26(21H, m), 0.85(3H, m) |

TABLE 5-continued $$CH_3(CH_2)nO-\underset{}{\underset{}{\bigcirc}}-CH_2CON\underset{}{\overset{R^1}{|}}CH_2COOEt$$

| Compd. | n | R$^1$ | formula | NMR spectrum (in CDCl$_3$, δ: ppm) |
|---|---|---|---|---|
| 3-b | 11 | Ph | C$_{30}$H$_{43}$NO$_4$ | 7.20(7H, m), 6.85(2H, m), 4.58:4.52(2H, s), 4.15 (2H, q, 7Hz), 3.90(4H, m), 3.55(2H, m), 1.65(2H, m), 1.25(21H, m), 0.85(3H, m) |
| 3-c | 11 | (4-Cl)Bz | C$_{31}$H$_{44}$NO$_4$Cl | 7.20(4H, m), 6.80(4H, m), 4.32:4.26(2H, s), 3.95 (4H, m), 3.54:3.42(2H, s), 1.65(2H, m), 1.26(21H, m), 0.86(3H, m) |
| 3-d | 11 | Ph(CH$_2$)$_3$— | C$_{33}$H$_{49}$NO$_4$ | 7.23(7H, m), 6.84(2H, m), 4.15(2H, q, 7Hz), 3.95(4H, m), 3.56(2H, m), 3.26(2H, m), 2.53(2H, m), 1.66(4H, m), 1.26(21H, m), 0.86(3H, m) |
| 3-e | 11 | Ph(CH$_2$)$_2$— | C$_{32}$H$_{47}$NO$_4$ | 7.20(7H, m), 6.82(2H, m), 4.18(2H, m), 3.95(4H, m), 3.56(4H, m), 2.79(2H, m), 1.65(2H, m), 1.26(21H, m), 0.88(3H, m) |
| 3-f | 11 | i-Bu | C$_{28}$H$_{47}$NO$_4$ | 7.15(2H, m), 6.82(2H, m), 4.15(2H, q, 7Hz), 4.03:3.97 (2H, s), 3.90(2H, t, 7Hz), 3.68:3.54(2H, s), 3.21(2H, m), 1.72(3H, m), 1.26(21H, m), 0.89(9H, m) |
| 3-g | 11 | Bz | C$_{31}$H$_{45}$NO$_4$ | 7.26(7H, m), 6.85(2H, m), 4.67:4.61(2H, s), 4.15(2H, q, 7Hz), 4.03:3.86(2H, s), 3.91(2H, t, 7Hz), 3.74: 3.63(2H, s), 1.66(2H, m), 1.26(21H, m), 0.87(3H, m) |
| 3-h | 11 | (3,4,5-MeO)Bz | C$_{34}$H$_{51}$NO$_7$ | 7.22(2H, m), 6.85(2H, m), 6.25:6.39(2H, s), 4.61: 4.56(2H, s), 4.17(2H, q, 7Hz), 3.68(4H, m), 3.81(3H, s), 3.77(6H, s), 1.65(2H, m), 1.27(21H, m), 0.87(3H, m) |
| 3-i | 11 | CH$_3$ | C$_{25}$H$_{41}$NO$_4$ | 7.16(2H, m), 6.82(2H, m), 4.14(2H, m), 4.05(2H, m), 3.91(2H, t, 7Hz), 3.70:3.58(2H, s), 3.04(3H, s), 1.66(2H, m), 1.26(21H, m), 0.88(3H, m) |
| 3-j | 13 | (4-COOMe)Bz | C$_{33}$H$_{47}$NO$_6$ | 8.13(2H, m), 7.26(4H, m), 6.87(2H, m), 4.70:4.63(2H, s), 4.13(2H, m), 4.02(4H, m), 3.77(3H, s), 3.62(2H, m), 1.65(2H, m), 1.27(21H, m), 0.87(3H, m) |
| 3-k | 11 | (thiophen-CH$_2$—) | C$_{29}$H$_{39}$NO$_4$S | 7.23(4H, m), 6.84(3H, m), 4.65:4.57(2H, s), 4.15 (2H, m), 4.04:3.92(2H, s), 3.91(2H, m), 3.76:3.61 (2H, s), 1.65(2H, m), 1.26(21H, m), 0.87(3H, m) |
| 3-l | 11 | (2,3,5,6-Me$_4$-4-OMe-C$_6$-OMe) | C$_{36}$H$_{55}$NO$_4$ | 7.24(2H, m), 6.84(2H, m), 4.72:4.55(2H, s), 4.09(2H, m), 3.88(4H, m), 3.58(3H, s), 3.54(3H, s), 2.17(9H, s), 1.65(2H, m), 1.24(21H, m), 0.87(3H, m) |
| 3-m | 13 | CH$_3$ | C$_{27}$H$_{45}$NO$_4$ | 7.20(2H, m), 6.85(2H, m), 4.14(2H, m), 4.05(2H, m), 3.91(2H, t, 7Hz), 3.71:3.60(2H, s), 3.05(3H, s), 1.61(2H, m), 1.26(25H, m), 0.88(3H, m) |

TABLE 6

$$CH_3(CH_2)nO-\underset{}{\underset{}{\bigcirc}}-CH_2CON\underset{COOC_2H_5}{\overset{X}{\diagup}}$$

| Compd. | n | X | formula | NMR spectrum (in CDCl$_3$, δ: ppm) |
|---|---|---|---|---|
| 3-n | 11 | CH$_2$ | C$_{27}$H$_{43}$NO$_4$ | 7.20(2H, m), 6.85(2H, m), 4.43(1H, m), 4.13(2H, q, 7Hz), 3.89(2H, t, 7Hz), 3.58(2H, m), 3.52(2H, m), 1.73(6H, m), 1.26(21H, m), 0.85(3H, m) |
| 3-o | 11 | s | C$_{26}$H$_{41}$NO$_4$S | 7.16(2H, d, 9Hz), 6.85(2H, d, 9Hz), 5.12(1H, t, 6Hz), 4.60(1H, d, 8Hz), 4.47(1H, d, 8Hz), 4.18(2H, q, 7Hz), 3.92(2H, t, 7Hz), 3.69(2H, s), 3.20(2H, d, 6Hz), 1.76(2H, m), 1.26(21H, m), 0.88(3H, m) |

REFERENCE EXAMPLE 6

In accordance with the procedure of Reference Example 5, octadecyloxyacetic acid was allowed to react with oxalyl chloride to give a corresponding acid chloride, which was allowed to react with N-(3,4,5-trimethoxybenzyl)glycine ethyl ester (2-h) to give N-(3,4,5-trimethoxybenzyl)glycine-N-octadecyloxyacetylglycine ethyl ester (3-p) as an oil.

Molecular formula: C$_{34}$H$_{55}$NO$_7$.

NMR spectrum (CDCl$_3$): 6.40 (2H,s), 4.58 (2H,m), 4.16 (2H, m), 3.86 (4H,m), 3.75 (9H,s), 3.45 (2H,m), 1.65 (2H,), 1.24 (33H, m), 0.85 (3H,m).

REFERENCE EXAMPLE 7

In accordance with the procedure of Reference Example 5, the compound (3-q to 3-t) listed in Table 6(II) were synthesized.

TABLE 6 (II)

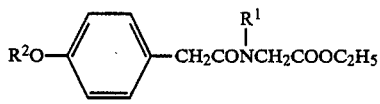

$$R^2O-\text{C}_6\text{H}_4-CH_2CONCH_2COOC_2H_5 \quad (R^1)$$

| Compd. | $R^1$ | $R^2$ | formula | NMR spectrum (in CDCl₃, δ: ppm) |
|---|---|---|---|---|
| 3-q | Me | 4-F—Bz | $C_{20}H_{22}NO_4F$ | 7.50~6.80(8H, m), 5.01(3H, s), 4.22(2H, q, 7Hz), 4.13:4.01(2H, s), 3.71:3.59(2H, s), 3.07:2.99(3H, s) 1.26(3H, t, 7Hz) |
| 3-r | $CO_2Et$ | $CH_3(CH_2)_9$ | $C_{26}H_{41}NO_6$ | 7.16(2H, d, 8Hz), 6.84(2H, d, 8Hz), 4.18(2H, s), 4.15(4H, m), 4.09(2H, s), 3.91(2H, t, 7Hz), 3.65(2H, s) 1.70(2H, m), 1.26(17H, m), 0.86(3H, m) |
| 3-s | (3,4,5,-triMeO)Bz | $CH_3(CH_2)_{17}$ | $C_{34}H_{59}NO_7$ | 6.47(2H, s), 4.71(2H, s), 4.17(4H, m), 3.96(2H, m), 3.88(9H, s), 3.60(2H, m), 1.70(2H, m), 1.26(33H, m), 0.88(3H, m) |
| 3-t | (3,4,5-triMeO)Bz | $CH_3(CH_2)_{13}$ | $C_{30}H_{51}NO_7$ | 6.47(2H, s), 4.70(2H, s), 4.16(4H, m), 3.96(2H, m), 3.86(9H, s), 3.57(2H, m), 1.65(2H, m), 1.26(25H, m), 0.87(3H, m) |

REFERENCE EXAMPLE 8

To a dichloromethane solution (50 ml) of 4-dodecycloxyphenylacetic acid (3.2 g, 0.01 mol) was added oxalyl chloride (2 ml). The solution was stirred for 30 minutes at room temperature and then for 30 minutes at 50° C., followed by concentration under reduced pressure. The concentrate was dissolved in dichloromethane (10 ml), which was added dropwise at 0° C. to a dichloromethane (50 ml) solution of trimethylamine (4 ml) and ethyl thioglycolate (1.2 ml, 0.01 mol). The solution was stirred at 0° C. for 2 hours, to which was added IPE (100 ml), followed by washing with water. The extract was dried and concentrated under reduced pressure. The concentrate was purified by means of silica gel chromatography (developing solvent: dichloromethane:hexane=1:1) to afford ethyl S-(4-dodecyloxyphenyl)acetylthioglycolate (3-u, 2.8 g, 66%).

Molecular formula : $C_{24}H_{38}O_4S$.

NMR spectrum (CDCl₃): 7.15 (2H,d,9 Hz), 6.82 (2H,d,9 Hz), 4.13 (2H,q,7 Hz), 3.90 (2H,t,7 Hz), 3.76(2H,s), 3.61 (2H,s), 1.73 (2H,m), 1.25(18H,m), 1.21 (3H,t,7 Hz), 0.86 (3H,m).

REFERENCE EXAMPLE 9

To a solution of ethyl phenylacetate (13.1 g, 0.08 mol) and aluminium chloride (24.5 g, 0.18 mol) was added undecanoyl chloride (20 ml) at −10° C. The reaction mixture was stirred for 20 minutes at room temperature and further for 4 hours at 50° C., and then poured into the mixture of concentrated hydrochloric acid (40 ml) and ice (160 g). The resultant precipitate was extracted with ethyl acetate, and the organic layer was washed with water, dried and concentrated under reduced pressure. The resulting residue was dissolved in ethanol (100 ml), to which was added sodium borohydride (1.18 g, 0.03 mol). The reaction mixture was stirred at room temperature, to which was added 1N hydrochloric acid and the mixture was extracted with ethyl acetate. The organic layer was washed with water, dried and concentrated under reduced pressure. The residue was purified by silica gel chromatography (developing solvent: hexane:ethyl acetate=5:1) to obtain ethyl 4-(1-hydroxyundecyl)phenylacetate (3-v, 10.9 g, 41%) as oil.

Molecular formula: $C_{21}H_{34}O_3$.

NMR spectrum (CDCl₃): 7.27 (4H,m), 4.63 (1H,t,7 Hz), 4.12 (2H,q,7 Hz), 3.57 (2H,s), 1.70 (2H,m), 1.25 (19H,m), 0.86(3H,m).

To the solution of ethyl 4-(1-hydroxyundecyl)-phenylacetate (9.7 g, 0.029 mol) in acetic acid (50 ml) was added 10%-palladium on carbon. The reaction mixture was stirred for 18 hours under 1 atmospheric pressure of hydrogen and then poured onto the mixture of concentrated ammonia water (100 ml) and ice (100 g). The resultant precipitate was extracted with ethyl acetate. The organic layer was washed with water, dried and concentrated under reduced pressure to obtain ethyl 4-undecylphenylacetate (3-w, 8.2 g, 88%) as an oil.

Molecular formula: $C_{21}H_{24}O_2$.

NMR spectrum (in CDCl₃): 7.15 (2H,m), 4.13 (2H,q,7 Hz), 3.55 (2H,s), 2.57(2H,t,8 Hz), 2.55 (2H,m), 1.27 (19H,m), 0.86 (3H,m).

To the solution of ethyl 4-undecylphenylacetate (7.2 g, 0.023 mol) in a mixture of methanol (40 ml) and tetrahydrofuran (40 ml) was added sodium hydroxide (2.2 g, 0.055 mol) and stirred at 50° C. for 20 minutes. The reaction mixture was adjusted to pH 4 with 2N hydrochloric acid after concentration. The resultant mixture was extracted with ethyl acetate, and the organic layer was washed with water, dried and concentrated under reduced pressure. The resulting crude crystals were recrystallized from hexane to obtain 4-undecylphenylacetic acid (3-x, 1.8 g, 27%). m.p. 83°–84° C.

Molecular formula: $C_{19}H_{30}O_2$.

NMR spectrum (in CDCl₃): 7.15 (4H,s), 3.59 (2H,s), 2.59 (2H,t,8 Hz), 1.10 (2H,m), 1.26 (16H,m), 0.87 (3H,m).

REFERENCE EXAMPLE 10

According to the method of Reference Example 5, 4-dodecyloxyphenylacetic acid was reacted with oxalyl chloride to obtain the corresponding acid chloride, which was reacted with diethyl aspartate to obtain diethyl N-(4-dodecyloxyphenylacetyl)aspartate (3-y).

Molecular formula: $C_{28}H_{45}NO_6$.

NMR spectrum (in CDCl₃): 7.15 (2H,d,9 Hz), 6.83 (2H,d,9 Hz), 6.43 (1H,d,9 Hz), 4.80 (1H,dt,5,9 Hz), 4.15 (2H,q,7 Hz), 4.08 (2H,q,7 Hz), 3.93 (2H,t,6 Hz), 3.51 (2H,s), 2.93 (1H,dd,5,17 Hz), 2.75 (1H,dd,5,17 Hz), 1.75 (2H,m), 1.27 (18H,m), 1.21 (3H,t,7 Hz), 1.16 (3H,t,7 Hz), 0.87 (3H,m).

To the solution of diethyl N-(4-dodecyloxyphenylacetyl)aspartate (2.0 g, 4.1 m mol) and methyl iodide (0.76 ml) in N,N-dimethylformamide (20 ml) was added sodium hydride (60% oil, 0.2 g, 4.8 m mol) under ice cooling and the resulting mixture was stirred for 30 minutes. A saturated aqueous solution of ammonium chloride (50 ml) was added to the reaction mixture and the mixture was extracted with IPE. The organic layer was washed with water, dried and concentrated under reduced pressure to obtain crude diethyl N-(4-dodecyloxyphenylacetyl)-N-methylaspartate (3-z).

Molecular formula: $C_{29}H_{47}NO_6$.

NMR spectrum (in $CDCl_3$): 7.13 (2H,m), 6.83 (2H,m), 4.90 (1H,m), 4.15 (4H,m), 3.91 (2H,t,6 Hz), 3.81:3.67 (2H,s), 3.01:2.78 (3H,s), 2.95 (2H,m), 1.75 (2H,m), 1.27 (24H,m), 0.87 (3H,m).

EXAMPLE 1

In a mixture of THF (50 ml) and DMF (10 ml) was dissolved ethyl N-(4-dodecyloxyphenylacetyl)-N-methylaminoacetate (4.0 g, 0.01 mol.). To the solution was added at room temperature potassium tertiary butoxide (1.8 g, 1.6 mol.) and the mixture was stirred for one hour, to which was then added 2N HCl (20 ml), followed by extraction with ethyl acetate. The organic layer was washed with water, dried and concentrated under reduced pressure to give crude crystals. The crude crystals were recrystallized from IPE - ethyl acetate to give N-methyl-3-(4-dodecyloxyphenyl)-4-hydroxy-3-pyrrolin-2-one (4-b, 2.4 g, 71%).

By the same procedure as above, compounds (4-a, 4-c to 4-t, 5-a to 5-g) were synthesized. Physico-chemical properties of them are shown in Table 7, 8, 9, 10 and 11.

TABLE 7

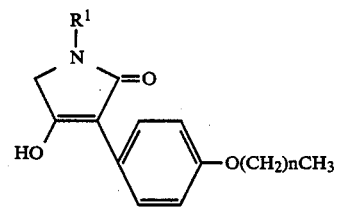

| Compd. | $R^1$ | n | formula MP(°C.) | NMR spectrum(δ: ppm) |
|---|---|---|---|---|
| 4-a | Me | 13 | $C_{25}H_{38}NO_3$ 169–170 | 7.89(2H, d, 9Hz), 6.81(2H, d, 9Hz), 3.93(2H, t, 7Hz), 3.87 (2H, m), 2.96(3H, s), 1.70(2H, m), 1.25(21H, m), 0.86(3H, m) |
| 4-b | Me | 11 | $C_{23}H_{35}NO_3$ 171–172 | 7.92(2H, d, 9Hz), 6.83(2H, d, 9Hz), 3.92(2H, t, 7Hz), 3.86 (2H, m), 2.92(3H, s), 1.70(2H, m), 1.28(18H, s), 0.86(3H, m) |
| A-b' | Me | 9 | $C_{21}H_{31}NO_3$ 184–185 | 7.89(2H, d, 9Hz), 6.83(2H, d, 9Hz), 3.94(2H, t, 7Hz), 2.94(3H, s), 1.71(2H, m), 1.24(14H, m), 0.88(3H, m) |
| 4-c | iso-Bu | 11 | $C_{26}H_{41}NO_3$ 167–168 | 7.90(2H, d, 9Hz), 6.83(2H, d,9Hz), 3.92(2H, t, 7Hz), 3.87 (2H, s), 3.13(2H, d, 7Hz), 1.77(3H, m), 1.24(18H, m), 0.85 (6H, d, 7Hz), 0.85(3H, m) |
| 4-d | Me(CH$_2$)$_{11}$ | 11 | $C_{34}H_{57}NO_3$ 190–191 | 7.90(2H, d, 9Hz), 6.80(2H, d, 9Hz), 3.93(2H, t, 7Hz), 3.85 (2H, s), 1.70(2H, m), 1.26(18H, s), 0.87(3H, m) |
| 4-d' | HOCOCH$_2$ | 9 | $C_{22}H_{31}NO_5$ 244–245 | 7.89(2H, d, 9Hz), 6.85(2H, d, 9Hz), 4.06(2H, s), 3.96(2H, s), 3.93(2H, t, 7Hz), 1.70(2H, m), 1.28(14H, m), 0.88(3H, m) |
| 4-e | Ph | 11 | $C_{28}H_{37}NO_3$ 236–237 | 7.98(2H, m), 7.80(3H, m), 7.33(1H, m), 7.50(1H, m), 6.80 (2H, m), 4.34(2H, s), 3.94(2H, t, 7Hz), 1.68(2H, m), 1.16 (18H, s), 0.87(3H, m) |
| 4-f | Bz | 11 | $C_{29}H_{39}NO_3$ 168–169 | 7.96(2H, d, 9Hz), 7.27(5H, m), 6.88(2H, d, 9Hz), 4.55 (2H, s), 3.93(2H, t, 7Hz), 3.78(2H, s), 1.64(2H, m), 1.26 (18H, s), 0.84(3H, m) |
| 4-g | Ph(CH$_2$)$_2$ | 11 | $C_{30}H_{41}NO_3$ 228–229 | 7.90(2H, d, 9Hz), 7.26(5H, s), 3.83(2H, d, 9Hz), 3.91 (2H, t, 7Hz), 3.77(2H, s), 2.81(2H, m), 1.70(2H, m), 1.25 (18H, s), 0.87(3H, m) |
| 4-h | Ph(CH$_2$)$_3$ | 11 | $C_{31}H_{43}NO_3$ 171–172 | 7.90(2H, d, 9Hz), 7.21(5H, m), 6.83(2H, d, 9Hz), 3.18 (2H, m), 3.35(2H, t, 7Hz), 2.58(2H, t, 7Hz), 1.77(4H, m), 1.24(18H, m), 0.85(3H, m) |
| 4-i | 3-Thienyl | 11 | $C_{27}H_{37}NO_3S$ 169–170 | 7.96(2H, d, 9Hz), 7.53(1H, m), 7.33(1H, m), 7.01(1H, m), 6.89(2H, d, 9Hz), 4.53(2H, s), 3.93(2H, t, 7Hz), 3.81 (2H, s), 1.70(2H, m), 1.25(18H, s), 0.85(3H, m) |
| 4-j | (4-COOMe)Bz | 11 | $C_{32}H_{41}NO_5$ 99–100 | 7.99(4H, m), 7.34(2H, d, 9Hz), 6.88(2H, d, 9Hz), 4.68(2H, s), 3.96(2H, t, 6Hz), 3.86(3H, s), 3.76(2H, s), 1.65(2H, m), 1.28(18H, s), 0.87(3H, m) |
| 4-k | (4-COOH)Bz | 11 | $C_{30}H_{39}NO_5$ 139–140 | 7.96(4H, m), 7.36(2H, d, 9Hz), 6.89(2H, d, 9Hz), 4.63 (2H, s), 3.94(2H, t, 7Hz), 3.84(2H, s), 1.70(2H, m), 1.25 (18H, s), 0.84(3H, m) |
| 4-l | (3,4,5-MeO)Bz | 11 | $C_{32}H_{45}NO_6$ 161–162 | 7.95(2H, d, 9Hz), 6.85(2H, d, 9Hz), 6.50(2H, s), 4.50(2H, s), 3.93(2H, t, 7Hz), 3.79(6H, s), 3.71(3H, s), 1.70(2H, s), 0.86(3H, m) |

TABLE 7-continued

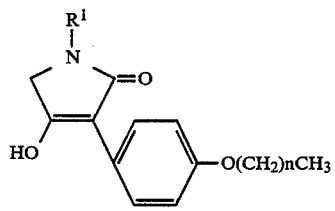

| Compd. | R[1] | n | formula MP(°C.) | NMR spectrum(δ: ppm) |
|---|---|---|---|---|
| 4-m | 2,5-di-Me, 3,6-di-Me, with 2,5-OMe (mesitylene-like with OMe) | 11 | $C_{34}H_{49}NO_5$ 167–168 | 7.91(2H, d, 9Hz), 6.83(2H, d, 9Hz), 4.56(2H, s), 3.93(2H, t, 7Hz), 3.60(3H, s), 3.55(3H, s), 3.27(2H, s), 2.16(3H, s), 2.14(6H, s), 1.71(2H, m), 1.24(18H, m), 0.85(3H, m) |
| 4-n | 4-ClBz | 11 | $C_{29}H_{38}NO_3Cl$ 194–195 | 7.94(2H, d, 9Hz), 7.32(4H, m), 6.86(2H, d, 9Hz), 4.54(2H, s), 3.92(2H, t, 7Hz), 3.79(2H, s), 1.71(2H, m), 1.25(18H, m), 0.85(3H, m) |

TABLE 8

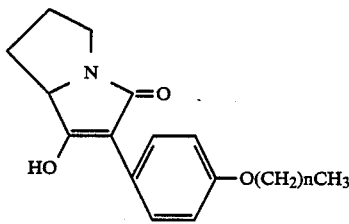

| Compd. | n | formula MP(°C.) | NMR spectrum (δ: ppm) |
|---|---|---|---|
| 4-o | 11 | $C_{35}H_{37}NO_3$ 168–169 | 7.86(2H, d, 9Hz), 6.82(2H, d, 9Hz), 4.25(1H, m), 3.91(2H, t, 7Hz), 3.30 (2H, m), 2.10(4H, m), 1.70(2H, m), 1.24(18H, m), 0.85(3H, m) |

TABLE 9

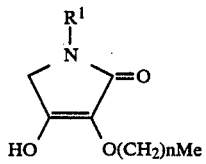

| Compd. | R[1] | n | formula MP(°C.) | NMR spectrum(δ: ppm) |
|---|---|---|---|---|
| 4-p | (3,4,5-MeO)Bz | 17 | $C_{32}H_{53}NO_6$ 188–119 | 6.43(2H, s), 4.35(2H, s), 3.92(2H, t, 7Hz), 3.74(6H, s), 3.63(3H, s), 3.57(2H, s), 1.65(2H, m), 1.26(30H, m), 0.86(3H, m) |
| 4-q | (3,4,5-MeO)Bz | 13 | $C_{28}H_{45}NO_6$ 123–124 | 6.47(2H, s), 4.36(2H, s), 3.94(2H, t, 7Hz), 3.76(9H, s), 3.75(2H, s), 1.80(2H, m), 1.28(22H, s), 0.88(3H, m) |

TABLE 10

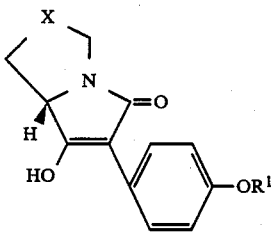

| Compd. | X | R[1] | formula MP(°C.) | NMR spectrum(in CDCl$_3$, δ: ppm) |
|---|---|---|---|---|
| 4-r | —CH(OH)— | CH$_3$(CH$_2$)$_{11}$ | C$_{25}$H$_{37}$NO$_4$ 212–214 | 7.87(2H, d, 9Hz), 6.85(2H, d, 9Hz), 5.10(1H, m), 4.50(1H, m), 4.38(1H, dd 6, 10Hz), 3.92(2H, t, 6Hz), 3.60(1H, dd, 5, 12Hz), 2.90(1H, d, 10Hz), 2.15(1H, dd, 5, 12Hz), 1.70(2H, m), 1.25(18Hz, m), 0.84(3H, m) |
| 4-s | —S— | CH$_3$(CH$_2$)$_{11}$ | C$_{24}$H$_{35}$NO$_3$S 188–190 | 7.85(2H, d, 9Hz), 6.85(2H, d, 9Hz), 4.80(1H, d, 10Hz), 4.48(1H, dd, 6, 8Hz), 4.04(1H, d, 10Hz), 3.93(2H, t, 6Hz), 3.29(1H, dd, 8, 11Hz), 2.89(1H, dd, 6, 11Hz), 1.65(2H, m), 1.25(18Hz, m), 0.84(3H, m) |
| 4-t | —S— | Bz | C$_{19}$H$_{17}$NO$_3$S 228(dec) | 7.86(2H, d, 9Hz), 7.40(5H, m), 6.98(2H, d, 9Hz), 5.09(2H, s), 4,84(1H, d; 10Hz), 4.49(1H, dd, 6Hz), 4.05(1H, d, 10Hz) 3.92(1H, dd, 8, 11Hz), 2.90(1H, dd, 6, 11Hz) |

TABLE 11

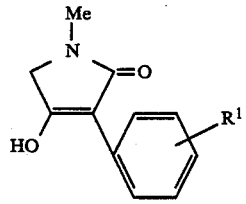

| Compd. | Position | R[1] | formula MP(°C.) | NMR spectrum(in CDCl$_3$, δ: ppm) |
|---|---|---|---|---|
| 5-a | p | (4-F)BzO | C$_{18}$H$_{16}$NO$_3$F 258–260 | 7.92(2H, d, 9Hz), 7.60–7.08(4H, m), 6.92(2H, d, 9Hz), 5.06(2H, s), 3.89(2H, s), 2.86(3H, s) |
| 5-b | p | (4-OMe)BzO | C$_{19}$H$_{19}$NO$_4$ 218(dec) | 7.91(2H, d, 9Hz), 7.37(2H, d, 9Hz), 6.95(4H, d, 9Hz), 5.00(2H, s), 3.88(2H, s), 3.75(3H, s), 2.86(3H, s) |
| 5-c | p | BzO | C$_{18}$H$_{17}$NO$_3$ 255(dec) | 7.95(2H, d, 9Hz), 7.42(5H, m), 6.95(2H, d, 9Hz), 5.08(2H, s), 3.88(2H, s), 2.86(3H, s) |
| 5-d | o | BzO | C$_{18}$H$_{17}$NO$_3$ 160–162 | 7.60–6.80(9H, m), 5.08:4.95(2H, s) 4.16:3.87(2H, s), 2.88:2.62(3H,s) |
| 5-e | m | BzO | C$_{18}$H$_{17}$NO$_3$ 213–214 | 7.75–7.10(8H, m), 6.79(1H, m), 5.04(2H, s), 2.89(2H, s), 2.85(3H, s) |
| 5-f | m | CH$_3$(CH$_2$)$_{11}$ | C$_{23}$H$_{35}$NO$_3$ 144–145 | 7.57(2H, m), 7.16(1H, t, 8Hz), 6.68(1H, m), 3.89(2H, s), 3.89(2H, t, 6Hz), 2.86(2H, s), 1.70(2H, m), 1.25(18H, m), 0.84(3H, m) |
| 5-g | p | CH$_3$(CH$_2$)$_{10}$ | C$_{22}$H$_{33}$NO$_2$ 179–180 | 7.85(2H, d, 9Hz), 7.11(2H, d, 9Hz), 3.84(2H, s), 2.96(3H, s), 2.56(2H, t, 7Hz), 1.60(2H, m), 1.26(16H, m), 0.86(3H, m) |

EXAMPLE 2

In a mixture of THF (50 ml) and DMF (10 ml) was dissolved ethyl S-(4-dodecyloxyphenyl)acetylthioglycolate (2.8 g, 6.6 m mol). To the solution was added at room temperature potassium tertiary butoxide (1.1 g, 10 m mol). The solution was stirred for one hour, to which was then added 2N HCl (20 ml), followed by extraction with ethyl acetate. The organic layer was washed with water, dried and concentrated under reduced pressure. The residue was purified by silica gel chromatography (developing solvent: ethyl acetate). The crude crystals obtained were recrystallized from IPE to obtain 2,5-dihydro-4-hydroxy-3-(4-dodecyloxyphenyl)thiophen-2-one (5-h, 13 mg, 0.5%).

m.p. 173°–175° C.

Molecular formula: C$_{22}$H$_{32}$O$_3$S.

NMR spectrum (in CDCl$_3$): 7.54 (2H,d,9 Hz), 6.85 (2H,d,9 Hz), 3.93 (2H,s), 3.93 (2H,t,6 Hz), 1.75 (2H,m), 1.27 (18H,m), 0.87 (3H,m).

EXAMPLE 3

By the procedure of Example 1, N-methyl-5-ethoxycarbonylmethyl-3-(4-dodecyloxyphenyl)-4-hydroxy-3-pyrrolin-2-one (5-i) was synthesized from diethyl N-(4-dodecyloxyphenylacetyl)-N-methylaspartate, m.p. 101°–102° C.

Molecular formula: C$_{27}$H$_{41}$NO$_5$.

NMR spectrum (in CDCl$_3$): 7.85 (2H,d,9 Hz), 6.85 (2H,d,9 hz), 4.25 (1H,dd,4,6 Hz), 4.03 (2H,q,6 Hz), 3.93 (2H,t,6 Hz), 3.00 (1H,dd,4,16 Hz), 2.80 (3H,s), 2.63 (1H,dd,6,16 Hz), 1.68 (2H,m), 1.25 (18H,m), 1.11 (3H,t,6 Hz), 0.86 (3H,,m).

EXAMPLE 4

To the solution of lithium diisopropylamide (1.1 m mol) in tetrahydrofuran (16 ml) was added N-methyl-3-(3-dodecyloxyphenyl)-4-hydroxy-3-pyrrolin-2-one (0.19 g, 0.5 m mol) at −78° C. and the mixture was stirred for 5 minutes at 0° C. The reaction mixture was cooled to −78° C. and, to this, was added benzaldehyde (0.15 ml, 1.5 m mol), stirring for 30 minutes. A saturated aqueous ammonium chloride solution (20 ml) was added to the reaction mixture and the resultant mixture was extracted with ethyl acetate. The organic layer was washed with water, dried and concentrated under reduced pressure. The resulting residue was purified by silica gel chromatography (developing solvent: ethyl acetate:hexane=1:1) to obtain two diastereomers of N-methyl-3-(3-dodecyloxyphenyl)-4-hydroxy-5-hydroxy-(phenyl)methyl-3-pyrrolin-2-one [diastereomer A (5-j): 0.10 g, diastereomer B (5-k): 0.05 g]. The former was recrystallized from IPE to give crystals of m.p. 117°–118° C. and the latter was recrysrtallized from methanol to give crystals of m.p. 110°–111° C.

Molecular formula: $C_{30}H_{41}NO_4$.

NMR spectrum (in $CDCl_3$):

Diastereomer A: 7.25 (8H,m), 6.72 (1H,m), 4.60 (1H,d,8 Hz), 3.87 (2H,t,7 Hz), 3.79 (1H,d,8 Hz), 2.18 (3H,s), 1.70 (2H,m), 1.27 (18H,m), 0.87 (3H,m)

Diastereomer B: 7.25 (8H,m), 6.75 (1H,m), 5.06 (1H,d,5 Hz), 3.98 (1H,d,5 Hz), 3.87 (2H,d,6 Hz), 2.69 (3H,s), 1.70 (2H,m), 1.27 (18H,m), 0.87 (3H,m).

What is claimed is:

1. A compound of the formula:

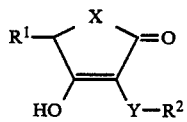

wherein

X is an imino group substituted with a primary or secondary $C_{1-6}$ alkyl, phenyl unsubstituted or substituted with hydroxyl, halogen, trihalogenomethyl, $C_{1-3}$ alkoxy, or $C_{1-3}$ alkyl; or phenyl-$C_{1-3}$ alkyl unsubstituted or substituted with halogen, trihalogenomethyl, methylenedioxy, $C_{1-3}$ alkyl, $C_{1-3}$ alkoxy, $C_{1-3}$ alkoxycarbonyl or carboxy; or thienyl or thienyl-$C_{1-3}$ alkyl group;

Y is a chemical bond, oxygen, phenylene, phenyleneoxy, or oxyphenyleneoxy;

$R^1$ is hydrogen, primary $C_{1-6}$ alkyl or phenyl unsubstituted or substituted with hydroxyl, phenyl or $C_{1-3}$ alkoxycarbonyl;

$R^2$ is primary $C_{6-20}$ alkyl or phenyl-$C_{1-3}$ alkyl wherein the phenyl is unsubstituted or substituted with hydroxyl, halogen, trihalogenomethyl, $C_{1-3}$ alkoxy or $C_{1-3}$ alkyl.

2. A compound of the formula:

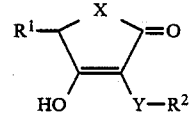

wherein

X is an imino group substituted with a $C_{1-15}$ alkyl, $C_{2-5}$ alkenyl or $C_{2-5}$ alkynyl;

Y is a phenyleneoxy;

$R^1$ is hydrogen, $C_{1-6}$ alkyl, $C_{2-6}$ alkenyl, $C_{2-6}$ alkynyl or phenyl which is unsubstituted or substituted with hydroxyl, phenyl or $C_{1-3}$ alkoxycarbonyl;

$R^2$ is $C_{6-20}$ alkyl, $C_{6-20}$ alkenyl, $C_{6-20}$ alkynyl or phenylalkyl wherein the phenyl is unsubstituted or substituted with hydroxyl, halogen, trihalogenomethyl, $C_{1-3}$ alkoxy or $C_{1-3}$ alkyl.

3. The compound according to claim 1, wherein X is imino substituted with $C_{1-6}$ alkyl which may be substituted with hydroxyl, $C_{1-3}$ alkoxy, halogen, carboxyl, $C_{1-3}$ alkoxycarbonyl.

4. The compound according to claim 1, wherein X is imino substituted with phenyl which may be substituted with hydroxyl, halogen, trihalogenomethyl, $C_{1-3}$ alkoxy or $C_{1-3}$ alkyl.

5. The compound according to claim 1, wherein X is imino substituted with phenyl-$C_{1-3}$ alkyl which may be substituted with halogen, trihalogenomethyl, methylenedioxy, $C_{1-3}$ alkyl, $C_{1-3}$ alkoxy, $C_{1-3}$ alkoxycarbonyl or/and carboxy.

6. The compound according to claim 1, wherein Y is a bond, ortho - or para-phenylene, meta- or para-phenyleneoxy or oxygen.

7. The compound according to claim 1, wherein $R^1$ is hydrogen.

8. The compound according to claim 1, wherein $R^2$ is $C_{6-20}$ alkyl.

9. The compound according to claim 1, wherein $R^2$ is phenyl-$C_{1-3}$ alkyl which may be substituted with halogen, $C_{1-3}$ alkyl or $C_{1-3}$ alkoxy.

10. The compound according to claim 1, wherein X is nitrogen atom substituted with $C_{1-3}$ alkyl or phenyl-$C_{1-3}$ alkyl, Y is meta- or para-phenyleneoxy, $R^1$ is hydrogen and $R^2$ is $C_{6-20}$ alkyl or phenyl-$C_{1-3}$ alkyl.

11. The compound according to claim 1, which is N-(3,4,5-trimethoxybenzyl)-3-(4-dodecyloxyphenyl)-4-hydroxy-3-pyrrolin-2-one.

12. The compound according to claim 1, which is N'-methyl-3-(4-dodecyloxyphenyl)-4-hydroxy-3-pyrrolin-2-one.

13. The compound according to claim 1, which is 3-(4-dodecyloxyphenyl)-4-hydroxy-N',5-methanothiomethano-3-pyrrolin-2-one.

14. The compound according to claim 1, which is 3-(4-benzyloxyphenyl)-4-hydroxy-N',5-methanothiomethano-3-pyrrolin-2-one.

15. A method of treatment of a circulatory disorder in a mammal with which comprises administration of a therapeutically effective amount of a compound of claim 1 and a pharmaceutically acceptable carrier, excipient or diluent therefor.

* * * * *